United States Patent
Tweedie et al.

(10) Patent No.: US 10,899,715 B2
(45) Date of Patent: *Jan. 26, 2021

(54) CONTINUOUS FLOW CARBOXYLATION REACTION

(71) Applicant: NOVARTIS AG, Basel (CH)

(72) Inventors: Scott Tweedie, Albany, NY (US); Sripathy Venkatraman, Albany, NY (US); James Zeller, Scottsdale, AZ (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,868

(22) Filed: Apr. 9, 2019

(65) Prior Publication Data

US 2019/0300485 A1     Oct. 3, 2019

Related U.S. Application Data

(63) Continuation of application No. 15/635,632, filed on Jun. 28, 2017, now Pat. No. 10,273,212, which is a continuation of application No. 14/866,085, filed on Sep. 25, 2015, now Pat. No. 9,725,413.

(60) Provisional application No. 62/055,286, filed on Sep. 25, 2014.

(51) Int. Cl.
   *C07D 217/04*     (2006.01)
   *B01J 19/24*      (2006.01)

(52) U.S. Cl.
   CPC ............ *C07D 217/04* (2013.01); *B01J 19/24* (2013.01); *B01J 19/242* (2013.01); *B01J 19/243* (2013.01); *B01J 2219/00099* (2013.01); *B01J 2219/0286* (2013.01); *B01J 2219/24* (2013.01)

(58) Field of Classification Search
   None
   See application file for complete search history.

(56) References Cited

U.S. PATENT DOCUMENTS

| 9,725,413 B2* | 8/2017 | Tweedie ............... B01J 19/24 |
| 2008/0183017 A1 | 7/2008 | Bender |
| 2014/0031387 A1 | 1/2014 | Zeller et al. |

FOREIGN PATENT DOCUMENTS

| JP | 2008179640 | | 8/2008 |
| WO | 2013086585 | A1 | 6/2013 |
| WO | 2014018748 | A1 | 1/2014 |
| WO | 2016049509 | A1 | 3/2016 |

OTHER PUBLICATIONS

International Search Report dated Dec. 28, 2015, corresponding International Application No. PCT/US2015/052320.
Pubchem. SID 187051834. Jul. 7, 2014, pp. 1-7 [online], [retrieved on Nov. 10, 2015]. Retrieved from the Internet <URL:https://pubchem.ncbi.nlm.nih.gov/substance/187051834.;p. 1; p. 3, formula.
Flint,S et al. The growth of Bacillus stearothermophilus on stainless steel. Journal of Applied Microbiology, vol. 90, 2001, pp. 151-157 [online], [retrieved on Nov. 10, 2015]. Retrieved from the Internet <URL:http://onlinelibrary.wiley.com/doi/10.1046/j.1365-2672.2001.01215.x/epdf.;abstract; p. 153, col. 2, paragraph 2.
Supplementary European Search Report dated Jan. 23, 2018 in connection with EPO No. 15844846.4.
Newby J.A., et al., "Design and Application of a Low-Temperature Continuous Flow Chemistry Platform" Organic Process Research & Development, Aug. 12, 2014, vol. 18(10), p. 1211 1220 (a document showing a well known technique).
Nagaki A, et al., "Extremely Fast Gas/Liquid Reactions in Flow Microreactors: Carboxylation of Short-Lived Organolithiums" Chemistry A European Journal, May 23, 2014, vol. 20(26), p. 7931 7934, S1 S11 (a document showing a well known technique).
Malet-Sanz L. and Susanne F., "Continuous Flow Synthesis. A Pharma Perspective" Journal of Medicinal Chemistry, 2012, vol. 55(9), p. 4062 4098 (a document showing a well known technique).
Jun. 25, 2019 Office Action issued in connection with JP No. 2017-516101.

* cited by examiner

*Primary Examiner* — Zinna Northington Davis
(74) *Attorney, Agent, or Firm* — Troutman Pepper Hamilton Sanders LLP

(57) ABSTRACT

The present invention is related to a two-step carboxylation reaction of an aryl group using continuous flow reaction conditions. This process permits large scale synthesis of useful reaction products in high yield.

9 Claims, 3 Drawing Sheets

CONTINUOUS FLOW CARBOXYLATION REACTION

CROSS-REFERENCE TO RELATED APPLICATIONS

This application is a continuation of U.S. application Ser. No. 15/635,632, filed Jun. 28, 2017, which is a continuation of U.S. application Ser. No. 14/866,085, filed Sep. 25, 2015, now U.S. Pat. No. 9,725,413, issued Aug. 8, 2017, which claims priority from U.S. Provisional Application No. 62/055,286, filed Sep. 25, 2014, the disclosures of which are hereby incorporated by reference in their entireties.

FIELD OF THE INVENTION

The present invention is related to a two-step carboxylation reaction of an aryl group using continuous flow reaction conditions. This process permits large scale synthesis of useful reaction products in high yield.

BACKGROUND OF THE INVENTION

Incorporation of a carboxyl acid to an aryl group by the addition of carbon dioxide to a Grignard or lithium anion is a well-known transformation that is widely used in chemical and pharmaceutical industries. While several major safety concerns have been reported on large scale for the formation of Grignard reagents or other organometallic species, it is still a common practice to form an organometallic species in a batch mode and subsequent quench with carbon dioxide. In general, most of these reactions are carried out at low temperatures and temperature extrusions during carbon dioxide quench due to inefficient mixing often leads to several by-products.

Compound 1, shown in scheme 1, is an intermediate used in the preparation of an active pharmaceutical ingredient (API). Several kilogram quantities of this intermediate are required to support the production of the API for early phase work. Compound 1 can prepared by adding carbon dioxide to lithium anion 3 which is generated from compound 2 at −78° C. in 75% yield. This reaction is sensitive to temperature and isolated yields are low from large scale runs with significant amounts of dark tar-like material isolated during the work up. In addition, several impurities are formed at higher temperature (>−65° C.) due to the instability of the anion. Such uncontrolled reactions on large scale can lead to the formation of reactive benzyne type intermediates which polymerize violently.

Scheme 1. Synthesis of Intermediate 1.

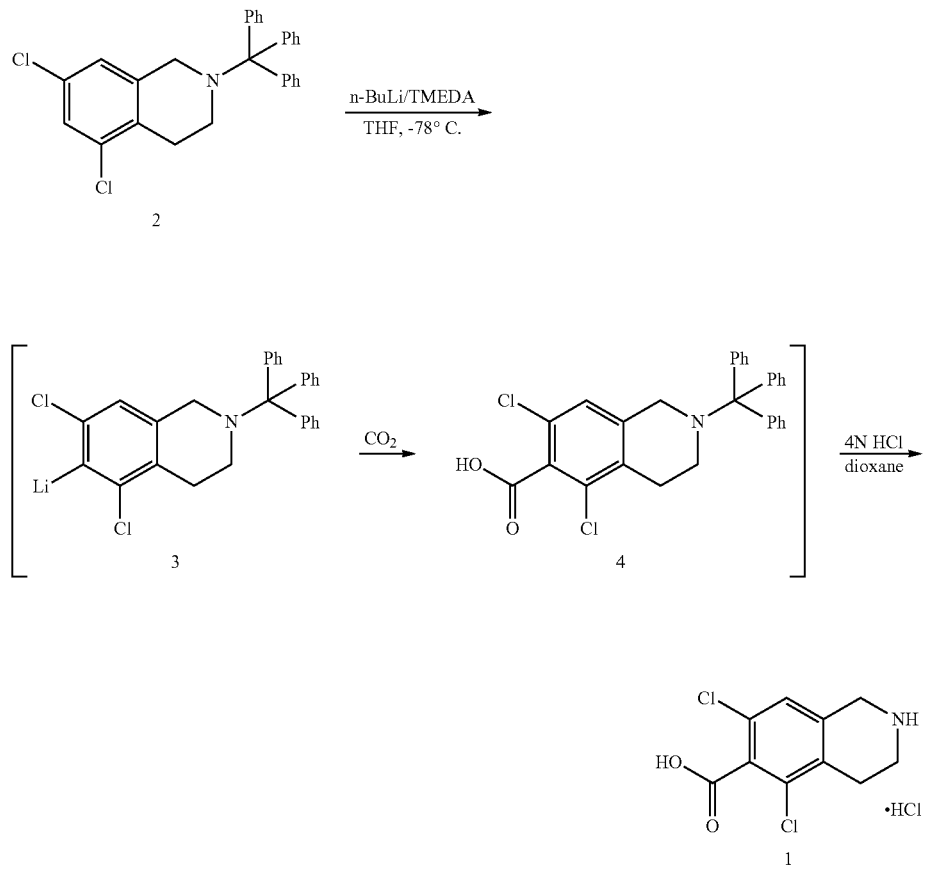

Accordingly, there is a great need in the art for new effective methods for synthesizing carboxylic acid intermediates in high yield and under conditions suitable for kilogram scale. This invention addresses these and other needs.

SUMMARY OF THE INVENTION

In some embodiments, the present invention relates to a process of preparing a compound of Formula I:

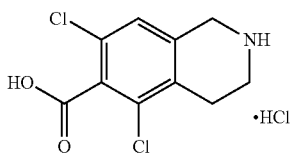

I comprising:
reacting a compound of Formula II:

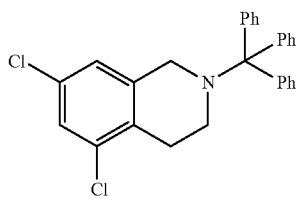

II with n-BuLi and TMEDA at −78° C. to afford a compound of Formula III:

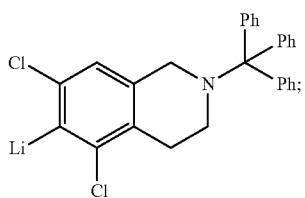

III quenching the compound of Formula III with gaseous carbon dioxide to afford a compound of Formula IV:

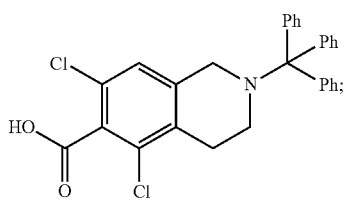

IV and
treating the compound of Formula IV with HCl to afford the compound of Formula I, wherein the method is performed using continuous flow reaction conditions.

In some embodiments, the step of reacting a compound of Formula II with nBuLi and TMEDA at −78° C. is performed in a polar aprotic solvent. In some embodiments, the polar aprotic solvent is THF.

In some embodiments, a reaction temperature is maintained at less than −65° C. during the quenching step with gaseous carbon dioxide.

In some embodiments, the step of reacting a compound of Formula IV with HCl is performed in a polar solvent. In some embodiments, the polar solvent is 1,4-dioxane.

In some embodiments, the HCl used in the reaction is 4N HCl.

The Formula I can be used, in some embodiments, as an intermediate in the synthesis of lifitegrast.

In some embodiments of the invention, the process is carried out in a continuous flow batch reactor. In some embodiments, the continuous flow batch reactor comprises stainless steel reactor tubes.

The present invention is also directed to a continuous flow batch reactor used for preparing the compound of Formula I under continuous flow reaction conditions.

DETAILED DESCRIPTION

The present invention provides an improved process for preparing the compound of Formula I using continuous flow chemistry. Applicants have surprisingly discovered that the inventive process facilitates: a) ease of performing low temperature reactions b) high mixing of the gas-liquid phase and c) excellent heat transfer capacity under flow conditions and d) consistent yield irrespective of the scale.

Batch Reaction

In one embodiment, the batch procedure for the carboxylation reaction involves the addition of BuLi (2.5 M solution) to a THF solution of 2 in the presence of TMEDA at −78° C. The lithium anion 3 is then quenched with gaseous carbon dioxide to afford the product. The addition of $CO_2$ to the reaction mixture is an exothermic reaction and controlled addition to maintain the batch temperature to <−65° C. can be used to minimize decomposition of the lithiated species and improve selectivity. In order to avoid temperature spikes with subsurface additions, a blanket of $CO_2$ is maintained. Since an in-process analysis of the anion is not practical, conversion can be monitored after quench with $CO_2$. Kinetic studies prior to translating to conditions can be done using an In-Situ ReactIR probe to ensure that both the anion formation and $CO_2$ quench are instantaneous.

Initial Reactor Design

Figure 1:
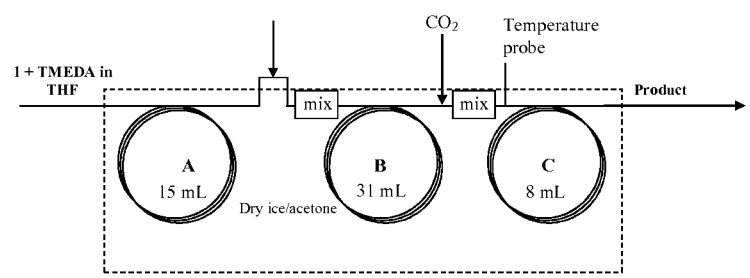
FIG. 1 shows a reactor of the invention.

In one embodiment, a reactor for use in the inventive process is shown in FIG. 1. As shown in FIG. 1, the reactor can contain three loops (A, B and C) where loop A is used to cool a mixture of 2 and TMEDA in THF to −78° C. Just after loop A, the base can be added and loop B can provide the necessary residence time for the anion formation after which carbon dioxide can be added as a gas which is passed through loop C to give the product. The entire reactor can be submerged into a dry ice acetone bath. In one embodiment, the loops are made of $\frac{1}{16}^{th}$ inch high density polyethylene (HDPE) tubing with two HPLC pumps for the reagents.

Figure 2A:
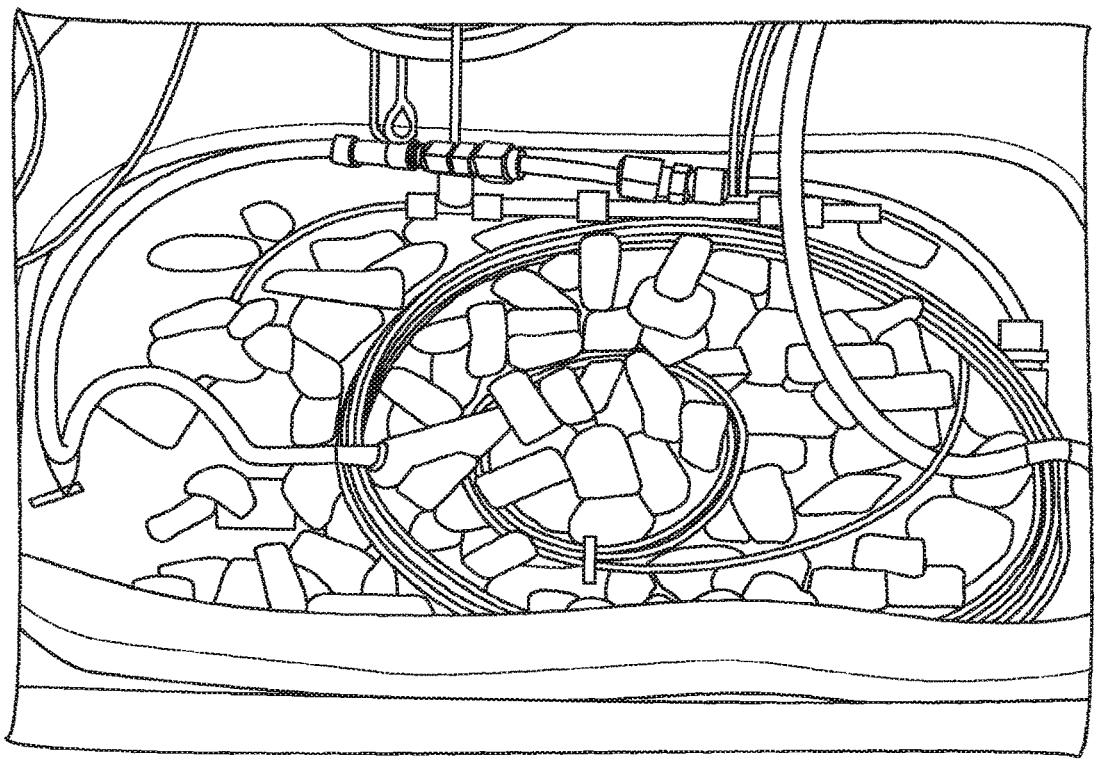
FIG. 2(A) shows a mixing unit for use in a reactor of the invention.
Figure 2B:
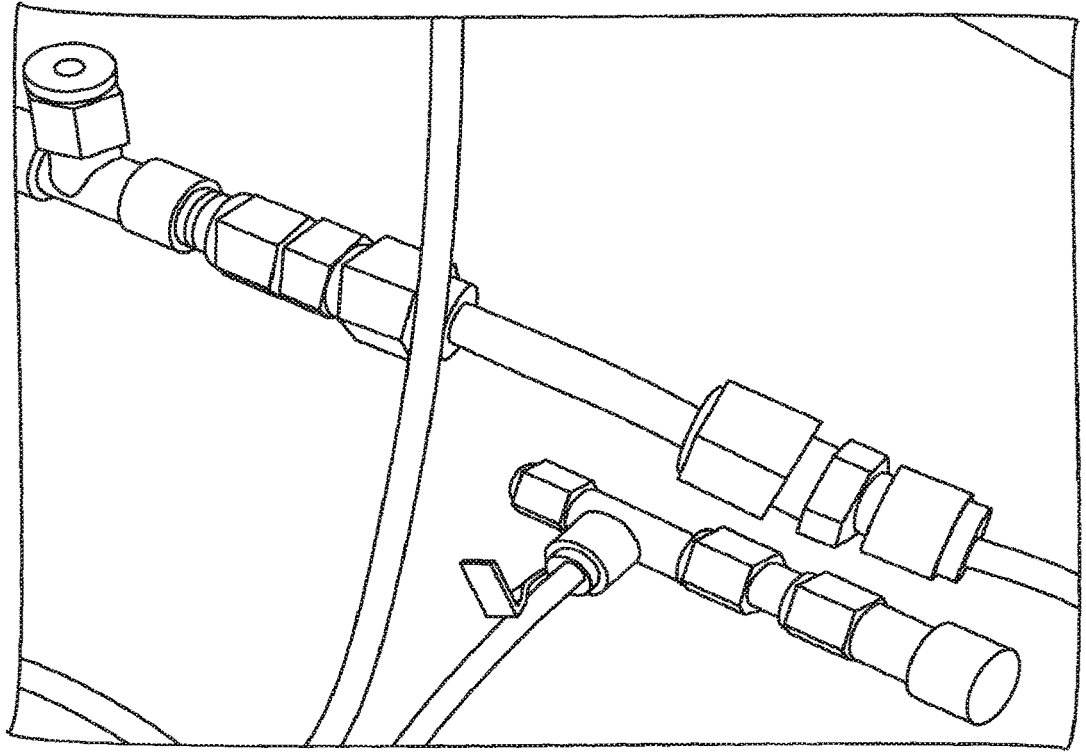
FIG. 2(B) shows an expanded view of the mixing unit.

In some embodiments, as shown in FIG. 2, the mixing units can consist of ¼" ID diameter tubing with two small stir bars trapped within. The stir bars can be agitated using a magnetic stir plate, providing turbulence sufficient for mixing of the reagents. In some embodiments, the back pressure unit at the end of the product stream can be set to 10 psi.

In some embodiments, the residence times for the trial runs are based on reaction monitoring in a batch mode (determined by HPLC analysis). Interestingly, addition of the base to 2 in THF is marked with a color change from pale orange to dark red, which decolorizes upon quench with carbon dioxide. The flow rates can be adjusted to achieve a base stoichiometry twice as the starting material. For the first few experiments, a small $CO_2$ cylinder can be directly connected to the flow reactor. The product stream can be collected after steady stage is achieved (the first one or two fractions can be discarded due to poor conversion) and worked up in a batch mode by quenching with 2N HCl, extraction with ethyl acetate and telescoping it to the next step to isolate 1.

Example 1. Optimizing Reaction Conditions of Carboxylation Reaction

This example was performed using the reactor and mixer units shown in FIGS. 1 and 2. As shown in Table 1, an experiment was carried out to optimize the flow rates and residence times during the carboxylation reaction. Increasing the residence time for the carbon dioxide quench from 1 minute to 5 minutes was found to provide a dramatic increase in the conversion. Commercially available 1.5 MBuLi varied significantly in quality from lot to lot and flow rate had to be adjusted accounting for the lower potency of the reagent. This issue was overcome using a 2.5 M solution which was much more consistent in quality. Conditions were further optimized by increasing the concentration of 2 in THF to 10% and lowering the residence time for the anion formation to 10 minutes which showed >90% conversion. In attempts to further improve the throughput to process larger quantities of material, the same set up was designed using ¼ inch ID HDPE tubing. The conditions optimized for the $\frac{1}{16}^{th}$ inch tubing were repeated and identical results were obtained.

TABLE 1

Optimization of the Carboxylation Reaction

| Scale (g) | Concentration of 2 in THF (%) | BuLi (M) | ID (inches) | Residence time (min) Anion formation | Residence time (min) $CO_2$ quench | HPLC Conversion |
|---|---|---|---|---|---|---|
| 5 | 6.7 | 1.5 | 1/16 | 17 | 1 | 55 |
| 5 | 6.7 | 1.5 | 1/16 | 17 | 5 | 90 |
| 30 | 10 | 2.5 | 1/16 | 10 | 5 | 93 |
| 100 | 10 | 2.5 | 1/4 | 10 | 5 | 96 |

However, it was noted that a HDPE tubing dipped in dry ice was not ideal for longer processing times as material leached out of the tubes to the coolant bath within a few hours of processing. Additionally, the lower temperatures made the tubing brittle and significant leaks were observed in the joints. Often butyl lithium froze in the addition port and caused significant back pressure. These issues along with the urgent need to process several kilogram quantities of material led us to redesign a more robust reactor that addressed these issues with a higher throughput capable of processing several kilogram quantities of material.

Example 2. Optimization of Reactor Design

In this Example, the reactor described in Example 1 was optimized. An identical unit as in Example 1 was prepared with the exception that stainless steel tubes were used instead of HDPE tubes. Since the heat exchange in the case of stainless steel is higher than HDPE tubes it was envisioned that a much lower residence time ($t_1$) would be required. The minimum tube length at maximum operatable flow rate required for complete heat dissipation was determined. If $l_1$ is the length needed to achieve the desired residence time and $l_2$ is the length needed for complete heat dissipation, then the tube length is considered as the higher of the two. The length $l_1$ is calculated based on the flow rate and the tube diameter. The length needed for complete heat dissipation ($l_2$) for a known flow rate can be calculated from the following equation:

$$Q = UA\Delta T_{lm}$$

Q—Heat Rate, BTU/hr; Q can be calculated according to the thermal properties of the process fluid (for process that has no reaction going on in the loop) or the enthalpy of the reaction occurred within the loop.

U—Heat Transfer Coefficient, BTU/(h-ft^2-F); U can be obtained according to literature data for known material construction of the tubing and the nature of the heat transfer media and the process fluid in the tubing.

A—Surface area, (ft^2); A can be expressed using the tubing length and the tubing internal diameter.

$\Delta T_{lm}$—logarithmic temperature difference between process fluid ($t_{in}$ and $t_{out}$) and the coolant ($T_{in}$ and $T_{out}$), ° F.

$$\Delta T_{lm} = \frac{(t_{in} - T_{out}) - (t_{out} - T_{in})}{\ln\left(\frac{t_{in} - T_{out}}{t_{out} - T_{in}}\right)}$$

Loop A is only a cooling loop and no heat is released from this operation. The length required to cool from ambient temperature to −78° C. was calculated. However, for the anion formation, heat of the reaction needs to be dissipated before the carbon dioxide quench. In the absence of this length, the carbon dioxide quench may be done at a higher temperature, out of the stability window for the anion. The heat of reaction was calculated by running an RCl experiment. Based on the heat that needs to be removed for loop A and B, the minimum length at the maximum flow rate to completely dissipate the heat was found to be 14 feet and 22 feet. The quench with $CO_2$ was the length needed for the reaction.

TABLE 2

Tube Length Calculations.

| Loop | Flow Rate (ml/min) | U (btu/h-ft^2-F) | Q (BTU/hr) | A (Ft^2) | Length (Ft) |
|---|---|---|---|---|---|
| A (Cooling) | 102 | 10 | 766 | 1.14 | 14 |
| B (Anion Formation) | 120 | 10 | 282.7 | 1.8 | 22 |
| C ($CO_2$ Quench) | >120 | — | — | — | — |

Figure 3A:
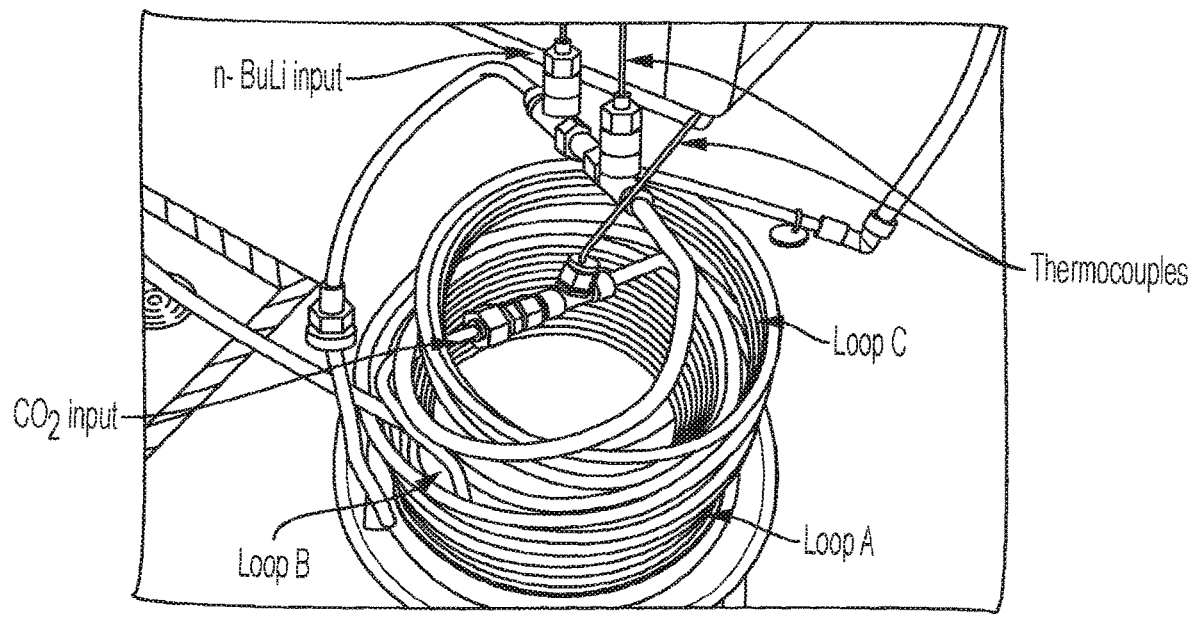
FIG. 3(A) shows stainless steel tubes for use in a reactor of the invention.
Figure 3B:
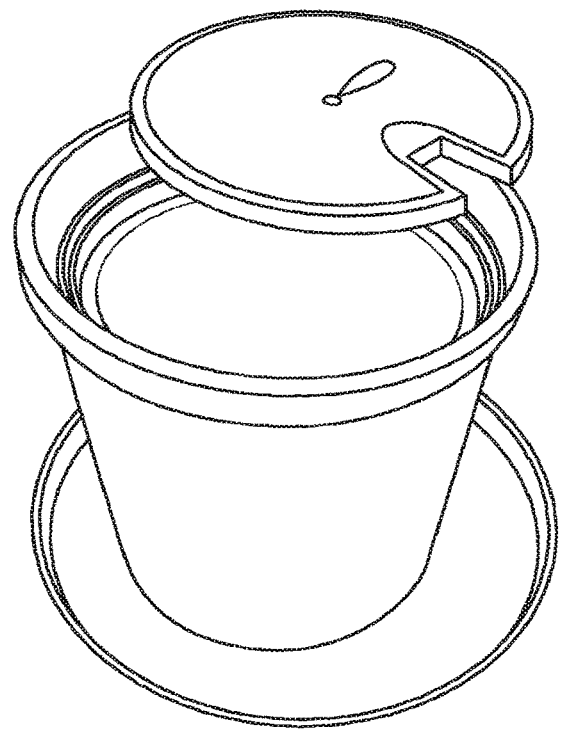
FIG. 3(B) shows a cooling compartments for the steel tubles.

Three tubes 5/16" diameter made of stainless steel were built (FIG. 3A), coiled and immersed into a carboy filled with dry ice acetone (FIG. 3B. Six static mixers were inserted into the tubes after both the anion formation and carbon dioxide quench to provide the required mixing.

Example 3. Scale Up Reaction Using Optimized Reactor. Generation Reactor Set-Up

In this Example, large-scale reactions were performed using the reactor prepared in Example 2. Since the mixing using static mixer was more efficient, Applicants were able to further reduce the residence time by increasing the flow rates. Table 3 summarizes the details of the scale up runs.

TABLE 3

Results of Scale-Up Runs.

| Entry | Scale (kg) | Residence Time (min) | | Purity (% AUC) | Yield Over Two Steps (%) |
| | | Anion Formation | CO$_2$ Quench | | |
| --- | --- | --- | --- | --- | --- |
| 1 | 5.4 | 2.0 | 0.9 | 91.6 | 81 |
| 2 | 3.5 | 2.0 | 0.9 | 94.4 | |
| 3 | 5 | 3.6 | 1.6 | 97.2 | 88 |
| 4 | 4 | 3.6 | 1.6 | 98.2 | 91 |
| 5 | 4 | 3.6 | 1.6 | 97.8 | |

As shown in Table 3, the residence time for the anion formation was reduced 3.6 minutes and carbon dioxide quench to 1.6 minutes which gave the highest purity of 1.

Only two minor issues with the synthesis were observed. For example, (1) during the synthesis, valeric acid (a byproduct of the reaction of BuLi with carbon dioxide whose freezing point is −20° C.) froze in the lines and stopped the flow. However, this occurred only when there was variation in the pumping rate of the reactants. This depended on the capacity of the pump on prolonged pumping. As long a study state was maintained, this issue was not observed; (2) commercially available BuLi contained significant amounts of residue and in the lack of a filter, the reagent ceased the pumps.

In conclusion, a two-step continuous flow carboxylation was developed and twenty two kilograms of material was successfully produced.

What is claimed is:

1. A process of preparing a compound of Formula I:

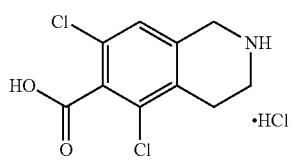

comprising:
reacting a compound of Formula II:

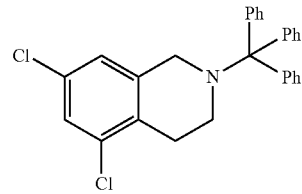

with n-BuLi and tetramethylethylenediamine at −78° C. to afford a compound of Formula III:

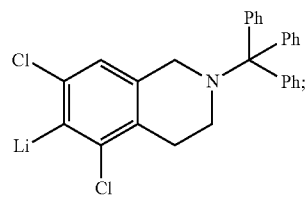

quenching said compound of Formula III with gaseous carbon dioxide to afford a compound of Formula IV:

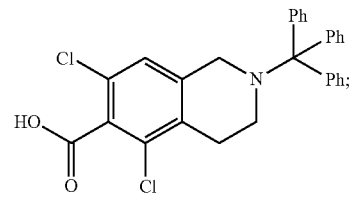

and
treating said compound of Formula IV with HCl to afford the compound of Formula I, wherein said method is performed using continuous flow reaction conditions, and wherein a reaction temperature is maintained at less than −65° C. during the quenching with gaseous carbon dioxide.

2. The process of claim 1, wherein said reacting a compound of Formula II with n-BuLi and tetramethylethylenediamine at −78° C. is performed in a polar aprotic solvent.

3. The process of claim 2, wherein said polar aprotic solvent is THF.

4. The process of claim 1, wherein said reacting a compound of Formula IV with HCl is performed in a polar solvent.

5. The process of claim 4, wherein said polar solvent is 1,4-dioxane.

6. The process of claim 1, wherein said HCl is 4N HCl.

7. The process of claim 1, wherein the compound of Formula I is an intermediate used in the synthesis of lifitegrast.

8. The process of claim 1, wherein said process is carried out in a continuous flow batch reactor.

9. The process of claim 8, wherein said continuous flow batch reactor comprises stainless steel reactor tubes.

* * * * *